United States Patent
Achenbach et al.

(10) Patent No.: US 8,301,264 B2
(45) Date of Patent: Oct. 30, 2012

(54) THERMAL THERAPY TEMPERATURE SENSOR CALIBRATION METHOD

(75) Inventors: Jonathan Achenbach, New York, NY (US); James E. Burgett, Maple Grove, MN (US); Claude Tihon, Eden Prairie, MN (US); Allen Putnam, Blaine, MN (US)

(73) Assignee: Urologix, Inc., Plymouth, MN (US)

( * ) Notice: Subject to any disclaimer, the term of this patent is extended or adjusted under 35 U.S.C. 154(b) by 682 days.

(21) Appl. No.: 12/387,045

(22) Filed: Apr. 27, 2009

(65) Prior Publication Data

US 2009/0276017 A1    Nov. 5, 2009

Related U.S. Application Data

(60) Provisional application No. 61/125,522, filed on Apr. 25, 2008.

(51) Int. Cl.
*A61F 2/00* (2006.01)

(52) U.S. Cl. ..................................... 607/100

(58) Field of Classification Search ............ 607/96–114; 606/27–31; 604/113–114
See application file for complete search history.

(56) References Cited

U.S. PATENT DOCUMENTS

| 4,860,752 | A | * | 8/1989 | Turner | 607/102 |
| 5,620,480 | A | * | 4/1997 | Rudie | 607/101 |
| 5,837,001 | A | * | 11/1998 | Mackey | 607/102 |

* cited by examiner

*Primary Examiner* — Manuel Mendez
(74) *Attorney, Agent, or Firm* — Dicke, Billig & Czaja, PLLC

(57) ABSTRACT

A thermal therapy of body tissue with electromagnetic energy is controlled by feedback from one or more temperature sensors placed in the vicinity of the tissue to be treated. The temperature sensors are calibrated by comparing stabilized temperature values of the one or more temperature sensors against a normal range of body temperature and adjusting sensed temperature to a value within a normal body temperature range if the actual temperature value of a stabilized temperature sensor is less than the normal body temperature range. The temperature adjustment to the temperature sensor is maintained throughout the thermal therapy which reduces the risk of thermal damage to healthy tissue located near the tissue to be treated.

3 Claims, 2 Drawing Sheets

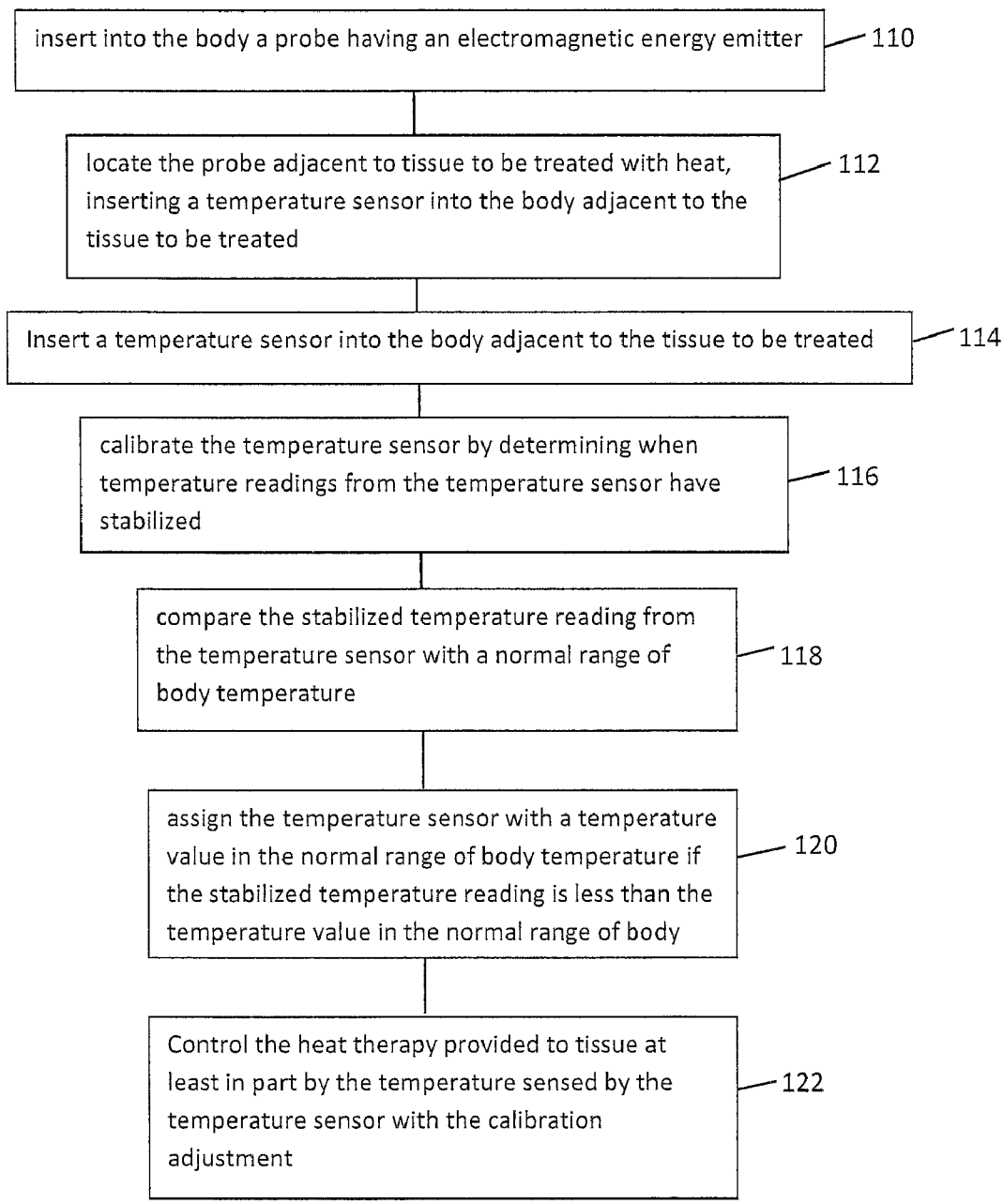

THERMAL THERAPY TEMPERATURE SENSOR CALIBRATION METHOD

CROSS-REFERENCE TO RELATED APPLICATIONS

This application claims the benefit of U.S. Provisional Patent Application Ser. No. 61/125,522, filed Apr. 25, 2008.

BACKGROUND

The present invention is a method of providing a thermal therapy to tissue in the body, and more specifically a method for calibrating one or more temperature sensors used in controlling a thermal therapy. It is known to delivery thermal therapy in various parts of the body with a probe that contains an electromagnetic energy emitter, i.e. an antenna. To ensure that the thermal therapy delivered is safe and effective, the temperature of the tissue being treated and/or the temperature of adjacent tissue not intended for treatment is typically monitored with one or more temperature sensors that are located in the vicinity of the treatment site.

It has been discovered that some patients have a lower than average core body temperature. Calibration of the one or more temperature sensors to temperatures below about average body temperature (e.g., 34.4-37.8 degrees Celsius) may result in excessive energy delivery to healthy tissue adjacent to tissue intended for treatment with a thermal therapy. In empirical studies involving transurethral thermal therapy of a variety disclosed in U.S. Pat. Nos. 5,330,518; 5,300,099; 5,370,677; 5,413,588; 5,733,319; 5,792,070; 5,843,144; 5,938,692; 6,007,571; 6,009,351; 6,032,078; 6,122,551; 6,161,049; 6,348,039; 6,490,488; and U.S. Patent Application Publication No. 2005/0222517, those patients with average core body temperature at or above a normal range have been discovered to be less likely to receive excessive energy delivery to the rectal wall. There is a need for an improved temperature sensor calibration method that takes into consideration the body temperature of the patient who is to receive a thermal therapy treatment.

SUMMARY OF THE INVENTION

A method of providing a heat therapy to tissue thus comprises placing an electromagnetic energy emitting probe adjacent to a first tissue region in the body that is intended to receive a thermal treatment adequate to thermally damage tissue in the first tissue region. A temperature sensor is placed adjacent to a second tissue region in the body, proximate to the first tissue region. The second tissue region is not intended to receive the thermal treatment. The temperature sensor is calibrated by monitoring temperature values of the temperature sensor for a time adequate to determine that the temperature sensor has attained a stabilized temperature value. The stabilized temperature value is compared against a predetermined value representative of a normal range of body temperature. If the stabilized temperature value is less than the predetermined value, the predetermined value is assigned to the temperature sensor. Electromagnetic energy is then delivered to the first tissue region to provide the thermal treatment while the temperature of the second tissue region is monitored with the temperature sensor. The amount of electromagnetic energy delivered to the first tissue region is decreased if the temperature sensed by the temperature sensor exceeds a predetermined threshold based on the temperature adjustment made during the calibration process.

BRIEF DESCRIPTION OF THE DRAWINGS

FIG. 2 is a flow diagram of a second embodiment of the method of the present invention.

DETAILED DESCRIPTION

Figure 1:
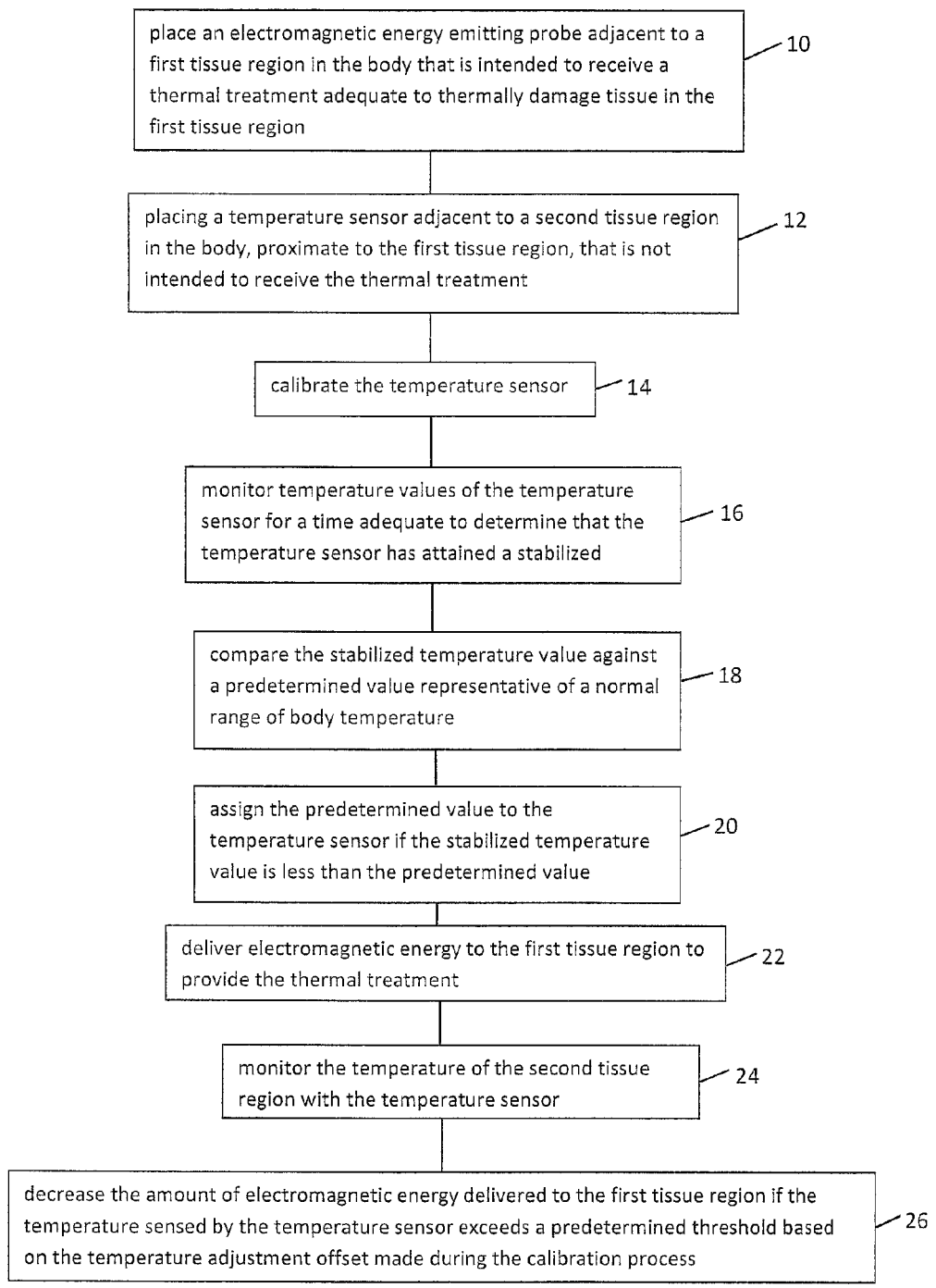
FIG. 1 is flow diagram of a first embodiment of the method of the present invention.

The present invention is a method for limiting the maximum amount (dose) of a thermal therapy for patients with low core body temperature readings. One example of thermal therapy is a transurethral thermal therapy of the prostate. One version of a known transurethral thermal therapy apparatus and control system is comprised of a control unit and a disposable procedure kit. The control unit contains a microwave generator, coolant pump, and all of the supporting electronics and software needed for therapy. The disposable procedure kit includes a coolant bag, a rectal thermosensing unit (RTU), and a microwave treatment catheter. One such commercially available system is the Targis System. Examples of such apparatus and systems and methods of using the same are fully described in one or more of the following U.S. Pat. Nos. 5,330,518; 5,300,099; 5,370,677; 5,413,588; 5,733,319; 5,792,070; 5,843,144; 5,938,692; 6,007,571; 6,009,351; 6,032,078; 6,122,551; 6,161,049; 6,348,039; 6,490,488; and U.S. Patent Application Publication No. 2005/0222517, the subject matter of which is incorporated herein in its entirety by reference.

One type of known microwave treatment catheter includes a fiber-optic temperature sensor, a microwave antenna, a connector and coaxial cable, coolant channels and connectors, a urine drainage channel and port, and a distal balloon for placement. Such a microwave treatment catheter is designed to be inserted into the urethra and to deliver microwave energy to the prostate tissue, while at the same time preventing overheating of the urethra, as fully described in the above-referenced patents.

One type of rectal thermosensing unit (RTU) is a catheter-based system that incorporates a compliant balloon and one or more temperature sensors used to monitor the patient's rectal temperature during a thermal therapy treatment. The RTU is placed in the patient's rectum prior to a treatment and left in place for the duration of the procedure. To avoid thermal damage to the rectal wall, which is in relatively close proximity to the prostate, the RTU will signal the control unit to discontinue or lower the microwave energy delivery to the microwave treatment catheter in the event that rectal temperatures are raised above 42.5 degrees Celsius.

Temperature sensors employed in a thermal therapy require calibration after they are inserted in the body. In the case of transurethral thermal therapy, after the microwave treatment catheter is properly positioned in the urethra and the RTU is properly positioned in the rectum, the respective temperature sensors are calibrated. It has been possible for physicians to initiate calibration of urethral temperature sensors before the rectal temperature sensor has fully stabilized to core body temperature. One prior calibration protocol sampled rectal temperature 20 times during a fixed 5 second period following insertion of a rectal temperature probe into the rectum. Calibration was deemed successful if the resulting average temperature was greater than 31.0 degrees C. and less than 42.5 degrees C. In an alternative calibration protocol, the average rectal temperature was sampled every 10 seconds and the difference from one sample to the next was required to be less than 0.3 degrees C. for calibration to be deemed successful. If the difference was greater than 0.3 degrees C., the temperature stabilization step continued sampling every 10 seconds until the difference from one sample to the next was less than 0.3 degrees C. The resulting rectal temperature average also had to be greater than 31.0 degrees C. and less than 42.5 degrees C. for the calibration to be deemed successful.

According to the present invention, healthy tissue adjacent to tissue intended to receive a thermal therapy is provided with one or more temperature sensors, which are calibrated according to a predetermined regimen that assesses a stabilized actual temperature reading of the body in the vicinity of the one or more temperature sensors, and adjusts the temperature of the one or more temperature sensors if actual stabilized temperature sensed is less than a predetermined normal range of body temperature. In one embodiment involving a transurethral thermal therapy of the prostate, rectal temperature is monitored by an RTU and is considered stabilized if the current rectal average temperature (one-second average reading) is within 0.1 degree Celsius of the previous 30 one-second average readings. Calibration is not successfully established until this requirement is met or until the rectal temperature sensor has been in place for at least seven minutes. If the stabilized temperature value of the RTU sensor(s) is less than a value within the normal range of body temperature, i.e., 34.4-37.8 degrees, an offset is added to the thermometry system to calibrate the RTU to a value within the normal range of body temperature. In one preferred embodiment, if the stabilized temperature of the RTU is less than 35.8 degrees Celsius, an offset is added to calibrate the RTU to a temperature of about 35.8 degrees Celsius.

Once the RTU temperature sensor is calibrated with the offset, the control unit functions as if the original starting core body temperature of the patient is the calibrated temperature. The offset is maintained throughout a thermal therapy procedure. For example, in one embodiment, if at calibration the actual RTU sensor readings are 35.5 degrees Celsius, the calibration temperature is set to 35.8 degrees Celsius. During a thermal therapy procedure, if the RTU sensor value reads 39.0 degrees Celsius, software in the control unit treats the value as 39.3 degrees Celsius as a result of the 0.3 degree offset made during calibration.

Three individual feedback PID control loops are commonly employed in control systems for a transurethral thermal therapy. A first PID control loop regulates microwave power to maintain the urethral temperature set point defined by the user, including the offset that may have been applied at calibration. In the example above with the 0.3 degree Celsius offset, the maintained urethral temperature will be 0.3 degrees Celsius cooler than it would have been without the offset. A second PID control loop regulates coolant temperature and is not affected by any offsets at calibration. A third PID control loop adjusts coolant temperature in reaction to the rectal temperature, including the offset that may have been applied at calibration. In the above example with the 0.3 degree Celsius offset, feedback from the third PID control loop will occur at a rectal temperature that is 0.3 degrees Celsius cooler than it would have been without the offset.

As shown in FIG. 1, in one embodiment, a method of providing a heat therapy to tissue thus comprises the following steps: At 10 an electromagnetic energy emitting probe is placed adjacent to a first tissue region in the body that is intended to receive a thermal treatment adequate to thermally damage tissue in the first tissue region. At 12 a temperature sensor is placed adjacent to a second tissue region in the body, proximate to the first tissue region. The second tissue region is not intended to receive the thermal treatment. At 14 the temperature sensor is calibrated. The calibration process includes at 16 the step of monitoring temperature values of the temperature sensor for a time adequate to determine that the temperature sensor has attained a stabilized temperature value. At 18 the stabilized temperature value is compared against a predetermined value representative of a normal range of body temperature. At 20 if the stabilized temperature value is less than the predetermined value, the predetermined value is assigned to the temperature sensor. At 22 electromagnetic energy is then delivered to the first tissue region to provide the thermal treatment while the temperature of the second tissue region is monitored with the temperature sensor at 24. At 26, the amount of electromagnetic energy delivered to the first tissue region is decreased if the temperature sensed by the temperature sensor exceeds a predetermined threshold based on the temperature adjustment offset made during the calibration process.

As shown in FIG. 2, in an alternative embodiment, a method of providing a heat therapy to tissue in the human body comprises the following steps: At 110 a probe having an electromagnetic energy emitter is inserted into the body. At 112, the probe is located adjacent to tissue to be treated with heat. At 114, a temperature sensor is inserted into the body adjacent to the tissue to be treated. Following the inserting step, at 116 the temperature sensor is calibrated by determining when temperature readings from the temperature sensor have stabilized. At 118, the stabilized temperature reading from the temperature sensor is compared with a normal range of body temperature. At 120, the temperature sensor is assigned with a temperature value in the normal range of body temperature if the stabilized temperature reading is less than the temperature value in the normal range of body temperature. Thereafter, at 122, the heat therapy provided to tissue is controlled at least in part by the temperature sensed by the temperature sensor with the calibration adjustment offset described above. The temperature sensor may be incorporated into the probe, or the temperature sensor may be located distant from the probe.

Although the present invention has been described with reference to exemplary embodiments, workers skilled in the art will recognize that changes may be made in form and detail without departing from the scope and spirit of the invention.

What is claimed is:

1. A method of providing a heat therapy to tissue, the method comprising:
   placing an electromagnetic energy emitting probe adjacent to a first tissue region in the body that is intended to receive a thermal treatment adequate to thermally damage tissue in the first tissue region;
   placing a temperature sensor adjacent to a second tissue region in the body, proximate to the first tissue region, that is not intended to receive the thermal treatment;
   calibrating the temperature sensor, the step of calibrating comprising:
      monitoring temperature values of the temperature sensor for a time adequate to determine that the temperature sensor has attained a stabilized temperature value;
      further comparing the stabilized temperature value against a predetermined value representative of a normal range of body temperature; and
      assigning the predetermined value to the temperature sensor if the stabilized temperature value is less than the predetermined value;
   delivering electromagnetic energy to the first tissue region to provide the thermal treatment;

monitoring the temperature of the second tissue region with the temperature sensor; and decreasing the amount of electromagnetic energy delivered to the first tissue region if the temperature sensed by the temperature sensor exceeds a predetermined threshold.

2. The method of claim 1 wherein the step of monitoring temperature values of the temperature sensor comprises:

recording the temperature sensed once each second; and comparing one recorded temperature to at least 30 previous recorded temperatures until the one recorded temperature is within 0.1 degrees Celcius of the 30 previous recorded temperatures.

3. The method of claim 1 wherein the step of monitoring temperature values of the temperature sensor comprises monitoring the temperature values for about seven minutes following the placing step.

* * * * *